United States Patent
Kocher et al.

(10) Patent No.: US 11,170,894 B1
(45) Date of Patent: Nov. 9, 2021

(54) ACCESS AND TEMPERATURE MONITORING SYSTEM (ATMS)

(71) Applicants: Robert William Kocher, McLean, VA (US); Douglas Earl Dyer, Herndon, VA (US); Loran Dean Ambs, Williamsburg, VA (US); John Shelly Bowling, II, Reston, VA (US)

(72) Inventors: Robert William Kocher, McLean, VA (US); Douglas Earl Dyer, Herndon, VA (US); Loran Dean Ambs, Williamsburg, VA (US); John Shelly Bowling, II, Reston, VA (US)

( * ) Notice: Subject to any disclaimer, the term of this patent is extended or adjusted under 35 U.S.C. 154(b) by 0 days.

(21) Appl. No.: 16/838,156

(22) Filed: Apr. 2, 2020

(51) Int. Cl.
| | | |
|---|---|---|
| *G16H 40/67* | (2018.01) | |
| *A61B 5/1171* | (2016.01) | |
| *A61B 5/01* | (2006.01) | |
| *G16H 50/30* | (2018.01) | |
| *A61B 5/00* | (2006.01) | |

(52) U.S. Cl.
CPC .............. *G16H 40/67* (2018.01); *A61B 5/01* (2013.01); *A61B 5/1171* (2016.02); *A61B 5/1176* (2013.01); *A61B 5/746* (2013.01); *G16H 50/30* (2018.01)

(58) Field of Classification Search
None
See application file for complete search history.

(56) References Cited

U.S. PATENT DOCUMENTS

| | | | | |
|---|---|---|---|---|
| 7,340,293 | B2 * | 3/2008 | McQuilkin | A61B 5/015 374/121 |
| 8,880,119 | B1 * | 11/2014 | Naghdi | H04M 1/72522 455/556.1 |
| 9,968,264 | B2 * | 5/2018 | Tzvieli | A61B 5/0077 |
| 10,045,699 | B2 * | 8/2018 | Tzvieli | A61B 5/004 |
| 10,154,810 | B2 * | 12/2018 | Tzvieli | A61B 5/163 |
| 10,307,104 | B2 * | 6/2019 | Horseman | A61B 5/4872 |
| 10,642,955 | B2 * | 5/2020 | Horseman | G16H 40/63 |
| 10,909,835 | B1 * | 2/2021 | Singh | G01J 5/04 |
| 2003/0204130 | A1 * | 10/2003 | Colston, Jr. | G16H 50/80 600/300 |
| 2004/0254472 | A1 * | 12/2004 | McQuilkin | A61B 5/015 600/473 |
| 2012/0319847 | A1 * | 12/2012 | Heller | A61B 5/0022 340/573.1 |
| 2013/0011819 | A1 * | 1/2013 | Horseman | A61B 5/4872 434/257 |

(Continued)

*Primary Examiner* — Chico A Foxx (57) ABSTRACT

The Access and Temperature Monitoring system (ATMs) checks the identity and health of persons seeking access to a facility, building, event, airport border, or controlled area. It quickly checks the person's identity by recognizing the person, for example, by facial recognition, or by reading a unique token the person has, such as a smart card. If the person seeking access is recognized, the system quickly checks the health of the person. For example, a contactless measuring of core temperature is taken and is then compared to an on-file core temperature of the individual to see if it is elevated. If elevated, a secondary check is made by a precision medical instrument and compared to the precision data on file. Networking ATMs together to an Access Control Center will further assist in identifying virus outbreaks and reduce response time to assist in saving lives.

11 Claims, 5 Drawing Sheets

(56) References Cited

U.S. PATENT DOCUMENTS

| | | | |
|---|---|---|---|
| 2013/0085409 A1* | 4/2013 | Heller | A61B 5/6887 |
| | | | 600/549 |
| 2013/0116591 A1* | 5/2013 | Heller | A61B 5/0077 |
| | | | 600/549 |
| 2013/0297217 A1* | 11/2013 | Bangera | G16H 50/20 |
| | | | 702/19 |
| 2014/0160432 A1* | 6/2014 | Brown, Jr. | A61B 3/113 |
| | | | 351/208 |
| 2016/0022219 A1* | 1/2016 | Crawley | G01J 5/30 |
| | | | 600/474 |
| 2017/0079532 A1* | 3/2017 | Larsen | G01J 5/0818 |
| 2017/0112671 A1* | 4/2017 | Goldstein | A61B 5/0205 |
| 2017/0150930 A1* | 6/2017 | Shikii | A61B 5/026 |
| 2017/0367660 A1* | 12/2017 | Shimada | G06Q 10/10 |
| 2018/0052970 A1* | 2/2018 | Boss | G16H 50/30 |
| 2018/0116578 A1* | 5/2018 | Tzvieli | A61B 5/318 |
| 2018/0150601 A1* | 5/2018 | Astigarraga | G06Q 50/01 |
| 2018/0242850 A1* | 8/2018 | Ellis | G01K 13/002 |
| 2019/0057317 A1* | 2/2019 | Malhotra | G01M 15/14 |
| 2019/0090816 A1* | 3/2019 | Horseman | A61B 5/7275 |
| 2019/0343397 A1* | 11/2019 | Meisal | A61B 5/6832 |
| 2019/0357857 A1* | 11/2019 | Tanaka | A61B 5/05 |
| 2020/0060553 A1* | 2/2020 | Tsuchimoto | A61B 5/0008 |
| 2020/0250356 A1* | 8/2020 | Santarone | G06F 30/13 |

* cited by examiner

FIG 1

| 42 | 43 | 44 | 45 | 46 | 47 | 48 | 49 | 50 | 51 | 52 | 53 |
|---|---|---|---|---|---|---|---|---|---|---|---|
| Name or ID no. | Date / Time | Org/ Location | Normal (Precision) | Alert Delta (Precision) | Alert Temp (Precision) | Normal (Screening) | Alert Delta (Screening) | Alert Temp (Screening) | Screening Measurement | Precision Measurement | Action |
| Bob Cook | 200325 1402 | no. 35 | 97.0 | 1.0 | 98.0 | 98.5 | .7 | 99.3 | 98.3 | none | none |
| Bob Cook | 200326 0802 | no. 43 | 97.0 | 1.0 | 98.0 | 98.5 | .7 | 99.3 | 99.4 | 96.9 | none |
| Bob Cook | 200327 0810 | no. 6 | 97.0 | 1.0 | 98.0 | 98.5 | .7 | 99.3 | 99.5 | 98.6 | Doctor |

| 54 | 55 | 56 | 57 | 58 | 59 | 60 | 61 | 62 | 63 | 64 |
|---|---|---|---|---|---|---|---|---|---|---|
| Location | Date / Time | Medical Alert | Type of Alert | Name or ID No. | Normal (Precision) | Measured (Precision) | Individual's Current Location | Individual's Previous Location | Previous Locations (N) | MISC. |
| BLD. A | 03/03/0830 | No | | Bob Cook | 97.5 | 97.3 | | | | |
| BLD. A | 03/04/0831 | No | | Bob Cook | 97.5 | 97.4 | | | | |
| BLD. A | 03/05/0832 | No | | Bob Cook | 97.5 | 98.0 | | | | |
| BLD. 26 | 03/09/0923 | No | | Bob Cook | 97.5 | 97.7 | | | | |
| BLD. 26 | 03/10/0925 | No | | Bob Cook | 97.5 | 97.8 | | | | |
| BLD. 35 | 03/11/0835 | No | | Bob Cook | 97.5 | 97.7 | | | | |
| BLD. 35 | 03/12/0900 | No | | Bob Cook | 97.5 | 98.2 | | | | |
| BLD. A | 03/13/0837 | ALERT! | Temparature | Bob Cook | 97.5 | 101.0 | Clarksburg WV | FBI HQ, DC | | |

FIG 5

ACCESS AND TEMPERATURE MONITORING SYSTEM (ATMS)

CROSS-REFERENCE TO RELATED APPLICATION

None

BACKGROUND OF THE INVENTION

Field of the Invention

The invention relates to the field of biometric identification. Specifically, the invention relates to the field of biometric identification of individuals and their location, as well as to determine their medical condition, and other metrics including where they have traveled, who they have come in contact with, their core body temperature, etc. in an attempt to identify individuals in areas of limited access, such as buildings, facilities, airports, border crossings, etc., (hereinafter "facility") so as to be able to identify individuals who should or should not be in the facility, as well as to obtain corroboration that the individual or individuals are authorized for access.

A primary consideration for persons to enter areas of a limited facility is validation of the identity of individuals requesting access or desiring to remain in the facility and corroboration that the person or persons requesting access or to remain in the facility are authorized for access.

Validation of identity has long been accomplished or augmented by facial recognition technologies. Comparing a visitor's identity validated by facial recognition against the list of persons authorized for entry to a facility is often a required step to allowing that person access to an otherwise restricted access point. However, validating identity and verifying identity against an authorized access list fails to consider other criteria for access, such as the mental and physical well-being of the individual seeking access.

Depending upon the nature of the restricted area, the state-of-health of an individual may be another criterion for granting access to a restricted area or to remain in the area. Readily measured indications of health or illness of visitors requesting access to restricted areas includes the body temperature of the visitor. Contactless, non-invasive measurement of the core temperature of an individual has long been accomplished by infrared (IR) devices implemented in the form of forehead thermometers and thermal imagers. Temperatures exceeding a preset threshold have been used as an indicator of fever associated with illness. Access to medically restricted or other areas would be granted only if measured temperature is below a pre-determined maximum.

Description of the Related Art

Temperature measurements compared to normal body temperature by prior-art methods fail to compensate for the error introduced by measuring the temperature of some exposed part of the body, which is necessarily cooler than the core temperature. Such techniques also fail to take into consideration the measurement bias of the non-contacting thermometer itself. Either or both of these two errors compromise the utility of this technique to accurately detect abnormal body temperature as an indication of ill health. Taken together, these two errors easily mask all but the most obvious indications of abnormal body temperature, which is indicative of fever or incipient illness. Even if these two errors are addressed, a further error of prior art methods of alerting on abnormal temperature is the inappropriate use of what is considered to be the "normal" body temperature.

It is well known in medical circles that comparison of a measured core temperature to a "normal" core temperature is not a simple exercise. While a temperature of 98.6° F. is widely considered as "normal" for the genera population, there is a great deal of variability depending upon the sensor used to measure the temperature and the location of measurement. Table 1 illustrates "normal" temperatures (±2 sigma) for several common measurement areas (Ng, et. al. and Geneva, et. al.).

TABLE 1

"Normal" core temperatures at various measurement locations (Ng et. al., and Geneva, et. al.).

| Measurement Location | Low (° F.) | High (° F.) | Delta (° F.) |
|---|---|---|---|
| Forehead | 87.8 | 96.1 | 8.3 |
| Axillary (under arm) | 95.0 | 98.5 | 3.5 |
| Tympanic (ear) | 96.4 | 99.5 | 3.1 |
| Oral | 96.3 | 99.3 | 3.0 |
| Rectal | 97.4 | 100.0 | 2.6 |

It is evident that the "normal" temperature of a population varies significantly with measurement technique and location. Depending upon measurement area, "normal" core temperature varies by 2.6° F. to 8.3° F. for healthy individuals in a large population. A clear trend in the data illustrates that the convenience of measuring core temperature and the accuracy of core temperature measurement are diametrically opposed; the least convenient measurement area produces the most accurate measurement. Because of the invasive nature of thermometers requiring contact with the skin or body cavities, contacting thermometers, despite their high accuracy, are incompatible of rapidly screening individuals seeking access to restricted areas. Therefore, prior-art techniques comparing body temperature measurement against large-population averages for normal body temperature are unable to accurately detect meaningful changes of state-of-health except in the most obvious circumstances.

Accuracy characteristics on contactless thermometers used in prior-art methods introduces additional errors limiting their usefulness for detecting indicators of ill health. Contactless core temperature sensors are conducive to rapid, non-invasive screening for health or illness of persons. Non-invasive techniques such as IR-based forehead thermometers are notoriously unreliable indicator of health of a visitor. Research published by the National Institutes of Health (Ng, et. al.) indicates that the normal temperature of healthy individuals measured by IR forehead thermometers varies between 87.8° F. and 96.1° F., a range of uncertainty of 8.3° F. Therefore, this study concludes that forehead temperature measured by contactless IR forehead thermometer in excess of 96.1° F. is suggestive of fever. Assuming a population average of 98.6° F. true core temperature, someone could have a core temperature greater than 105° F. (a symptom of influenza such as COVID-19) and register below the recommended threshold of fever indicated by contactless IR forehead thermometer. In addition to poor reliability, IR forehead thermometers require the patient to be still while data is collected for several seconds at near-contacting distances such as 4 to 5 inches. Therefore, IR forehead thermometers are inappropriate for assessing the state-of-health of persons seeking admittance to restricted areas. The temperature measurements produced by IR forehead thermometers introduce considerable ambiguity in body temperature and they do not support on-the-move temperature screening at an access point to a restricted area.

IR imaging techniques for measuring core temperature have been described in US PUB 2013/0215928, US PUB 2019/0192010, WO 2004/110248, and US PUB 2019/0357857. The advantage of this prior-art technique is that it allows contactless temperature measurements to be made on-the-move. In most implementations of this technique, areas around the eye, such as the medial canthus and ethmoid sinus, have produced temperature measurements that are within 3.24±1.44° F. of core temperature. While much better than measurements obtained by IR forehead thermometers, this technique also fails to provide the accuracy necessary to reliably detect abnormal core temperature within several degrees. IR imaging alone is not adequate for screening the health of individuals seeking entry to restricted access areas or to remain in certain access areas.

Considering the range of accuracy of the instruments themselves and the variability of individual data samples, there is significant uncertainty in the utility of prior-art methods of using a single sensor modality to provide temperature measurement as an indication of the state-of-health of individuals seeking access to or remain in restricted areas. Hence, multi-modal temperature sensing is a common solution; primary screening is conducted with a very convenient, low accuracy thermometer followed by secondary measurement with a more accurate, less convenient thermometer if the primary method raises doubt about the health of the person seeking entry to a restricted access area (Nguyen, et. al.).

Examples of accurate contacting thermometers include glass and liquid thermometers, liquid crystal strips that change color and electronic thermometers. These medical-precision thermometers measure core temperature at one of several common measurement areas such as the mouth, the ear, under the arm or rectum. This multi-modal, two-stage technique of collecting temperature data from an individual at a particular point in time is a compromise of both convenience and accuracy. Comparison of the individual's measured temperature and "normal" temperature of the general population still allows for uncertainty of several degrees; a sufficiently large uncertainty to hide an elevated temperature a few degrees. Prior-art methods that employ on-the-move, low-accuracy temperature screening combined with high-accuracy, inconvenient contacting temperature measurement fails to provide accurate indications of the state-of-health of individuals without establishing the body temperature normal for the individual being screened.

As was seen in Table 1 above, temperature variations between individuals varies by up to 3 degrees. The normal temperature of a healthy individual routinely varies by 1-2° F. during a day. These variations are largely controlled by an individual's metabolism and circadian rhythm, reproductive cycles, and season of year (Kelly, 2006), referred to below. The "normal" temperature for an individual can be established by multiple measurements at differing times of day over many days. Such long-term data enables the construction of a predictive model based on the individual's core temperature history (US PUB 2007/0161921). Once established, the model enables a much more accurate comparison of the individual's normal core temperature and the temperature measured at an entry control point. Under such circumstances, differences on the order of one degree can be meaningful. Prior-art methods of collecting temperature measurements to assess the state-of-health of individuals seeking access to or to remain in restricted access areas failed to take into consideration the temperature differences induced by the uniqueness of an individual's normal body temperature and the time-dependent fluctuations of body temperature. Therefore, prior art-methods were insensitive to meaningful changes in observed temperatures of individuals.

REFERENCES CITED

U.S. Pat. No. 5,991,429; Facial Recognition for Security Access and Identification.
U.S. Pat. No. 8,499,164; Biometric Authentication Utilizing Unique Biometric Signatures and Portable Electronic Devices.
US PUB 2015/0088776; Apparatus, System and Method Supporting Compliance with Customs/Border Requirements.
US PUB 2013/0215928; Method and Device for Measuring the Internal Body Temperature of a Patient.
Business Insider, 15 Feb. 2020; *Thermometer guns used to screen for coronavirus are 'notoriously' unreliable experts say, warning about improper use and false temperatures.*
Science Magazine, 13 Mar. 2020; *Airport screening is largely futile, research shows* PloS ONE, Vol. 6, Issue 1, January 2011; *Thermal Image Scanning for Influenza Border Screening: Results of an Airport Screening Study.*
American Journal of Infectious Control (Ng et. al.), 2005 May, 33(4):227-9; *A brief report on the normal range of forehead temperature as determined by noncontact, hand-held infrared thermometer.*
Open Forum Infectious Diseases, Geneva, et al., Published online Apr. 9, 2019; *Normal Body Temperature: A Systematic Review.*
Emerging Infectious Diseases Journal—CDC (Nguyen, et. al.), Volume 16, Number 11, November 2010; *Comparison of 3 Infrared Thermal Detection Systems and Self-Report for Mass Fever Screening.*
U.S. Pat. No. 9,470,584; Method and Apparatus for Accurate Detection of Fever.
FLIR website, 21 Mar. 2020, Thermal Imaging for Detecting Elevated Body Temperature, https://www.flir.com/discover/public-safety/thermal-imaging-for-detecting elevated-body-temperature/.
Alternative Medical Review. 2006 December; 11(4):278-93, Greg Kelly, N D; *Body Temperature Variability (Part 1): A Review of the History of Body Temperature and its Variability Due to Site Selection, Biological Rhythms, Fitness; and Aging.*

SUMMARY OF EXEMPLARY EMBODIMENTS OF THE INVENTION

According to an exemplary embodiment, the networking together of components of prior art systems and coupling that with individual health data, date-time group and location of the individual creates a new capability to provide the ability to respond to a health crisis with visibility never known before. An exemplary embodiment of this system checks the identity and health of persons seeking access to or seeking to remain in a restricted area. It quickly checks the person's identity by recognizing the person, for example, by facial recognition, or by reading a unique token the person has, such as a smart card. If the person seeking access is recognized, the system quickly checks the health of the person by measuring some health indicator such as whether or not the person has an elevated temperature. If the quick assessment of the person's health indicates possible illness, the system alerts an operator or otherwise guides the person to get a more accurate health assessment; in order for access or the ability to remain at the facility, is granted. If the more accurate health assessment indicates illness, then the person is denied entry via an operator, alert or other method and is directed instead to seek medical treatment; without which, access cannot be granted. The seeking of medical treatment may be voluntary or involuntary. For each identified person, the system retains records in a database to include the person, the system location, measurement resulting from a quick health assessment, measurements resulting from an accurate health assessment (if any), and the time. These records provide a baseline of normal health measurements for each person, and they are used to more precisely determine when that person may be ill. In addition, obtained records are shared with other locations to alert other persons in the case that a previously healthy person is found to be ill. Finally, the records are shared with authorities to assist medical researchers in understanding the spread of illness and also to inform governmental regulators and provide review of guidelines aimed at reducing the spread of serious illness. The system performs identification and the quick health assessment in a few seconds and with minimal effort by an operator and persons seeking access or to remain in the facility.

Although temperature approximation is achievable on all objects that emit thermal radiation, consideration must be taken to accurately estimate a human's body temperature for reasonable screening. Human skin is cooler on average than the human body's core temperature and varies greatly across the surface area of the body and under different conditions. Modern Infrared Thermography (IRT) approaches have identified several points external to the human body that can be used to estimate core temperature to a reasonable degree. One such solution is the measurement of thermal radiation from the forehead. This is a common application of IRT in low-cost consumer devices for temperature estimation. Temples have also been used as an alternative to the direct forehead.

While infrared thermography is more widely known for object temperature approximation, as opposed to precise medical applications, tympanic thermometers or in-ear thermometers, are widely used and medically certified devices which measure thermal radiation from the tympanic membrane within the ear canal.

Many different devices may be used for core temperature measurement including those with a digital display that make it easy for a human to read but have no electrical interface to a computer system. These devices may provide core temperature measuring to a computer by having the computer obtain an image of the device display and applying an optical character recognition (OCR) algorithm to the image. In this way, a computer, equipped with a camera, can use a video feed from the camera to automatically read a temperature displayed from such a device. Additionally, commercial thermal cameras typically offer the ability to offload captured images with temperature measuring embedded in the images, thus enabling the use of OCR to record the data. Alternatively, the user can type the temperature into a dialog box in system software, or the user could enter the information using a speech-to-text interface.

In other cases, a temperature measuring device can communicate directly with a computer using wired or wireless communication methods. A datalink between a temperature sensor and ATMs is achievable through a variety of methods based on the selected sensor's configuration and thus the system is not directly dependent on any one particular device. A discrete infrared sensor without the auxiliary infrastructure associated with enclosure, power, data storage, display and user interface of a commercial, off-the-shelf solution, bare-metal infrared sensor may be used as opposed to an off-the-shelf solution, which would provide a constant data stream over a standard protocol such as inter-integrated circuit (I2C) or serial peripheral interface (SPI). Commercial grade devices including both infrared thermometer guns and thermal cameras offer varying degrees of data offloading capabilities that can be used to establish a link with ATMs. An alternative embodiment of the ATMs relates to crowd monitoring. This exemplary embodiment enables screening of persons transiting an unobstructed passageway such as a sidewalk or hallway. In this embodiment, the identity collection device and the contactless medical collection device (a screening node) are covertly or overtly mounted in such a way to collect data from people transiting the passageway. Multiple screening nodes may be networked to provide enhanced awareness of larger areas of surveillance.

It is well-known that the normal internal core temperature varies with the individual, and it follows from thermodynamics that temperatures measured outside the core which approximate internal core temperature must also vary with the individual. As a result, to determine when a particular person has an elevated core temperature, it's important to know what the normal, healthy temperature of that person is. ATMs identifies a person and measures that person's temperature at about the same time. Recording this information in a database provides a baseline of normal temperature for that person, which is very helpful in detecting elevated core temperature for that person. A high temperature over some user-selected threshold warrants appropriate action such as switching to a more precise temperature measurement, denial of access, or medical treatment.

In addition, recording core temperature over time gives an indication of the relative health of the person and some understanding of whether a sick person is progressing or regressing in recovery. This information is also helpful beyond having only the current temperature. If the temperature records for a person indicate a rapid rise in temperature, then that may warrant appropriate action such as switching to a more precise temperature measurement, denial of access, or medical treatment. The database of temperatures-over-time for a set of persons can also include location information, and that information may be shared across the proposed system to provide illness tracking data that is helpful to authorities.

Authorities can use illness tracking data to make good decisions about travel restrictions or medical logistics. Illness tracking data may also be used to alert persons who may have been in contact with a sick person. Finally, illness tracking data may be helpful to medical researchers to verify or discount hypotheses and for other purposes.

LIST OF REFERENCE NUMERALS FOUND IN THE DRAWINGS

Element 1 represents an identity collection device.
Element 2 represents the data communication means for conveying identification information.
Element 3 represents a computer containing the database and links to all devices.
Element 4 represents a signal from the computer to the access approved signal.
Element 5 represents the access approved signal.
Element 6 represents the contactless medical collection device.
Element 7 represents the image or data collected from person to determine medical condition such as temperature, exhaustion, drug impairment, intoxication, mental condition, O2 levels, heart rate, heart condition, odor, etc.
Element 8 represents the signal from the computer to the medical condition results signal.
Element 9 represents the medical condition results signal.
Element 10 represents the precision medical condition measuring device.
Element 11 represents the communication link from the precision medical condition measuring device to the computer.
Element 12 represents an individual seeking access.
Element 13 represents the database in the computer.
Element 14 represents a determination that the person has not been identified as being in the database.
Element 15 represents the option to deny access or conduct a medical check from the precision medical reader.
Element 16 represents a match of the person in the database.
Element 17 represents to identify the identified person's screening alert temperature limit.
Element 18 represents comparing the person's screening alert medical condition limit to the real time medical condition reader from the contactless sensor.
Element 19 represents actions if the person is under the limit.
Element 20 represents logging data such as date-time group, location, and medical condition and allow access.
Element 21 is actions taken if the person is over the screening limit.
Element 22 is to identify the precision medical condition limit.
Element 23 represents comparing the person's precision alert medical condition limit to the real time medical condition reading from the precision medical sensor.
Element 24 represents action if person is under precision medical sensor limit.
Element 25 represents action to allow access and log date-time, location, and precision medical condition.
Element 26 represents actions should the person be over the precision medical sensor limit.
Element 27 represents possible option to respond if a person is over the temperature limit.
Element 28 represents Location 1 of an ATMs.
Element 29 represents Location 2 of an ATMs.
Element 30 represents Location 3 of an ATMs.
Element 31 represents Location 4 of an ATMs.
Element 32 represents Location N of N ATM.
Element 33 represents an Access Control Center server that receives, stores, and analyzes persons at various locations and health status.
Element 34 represents the ATMs data input to the ACC.
Element 35 represents the ATMs data input to the ACC.
Element 36 represents the ATMs data input to the ACC.
Element 37 represents the ATMs data input to the ACC.
Element 38 represents the ATMs data input to the ACC.
Element 39 represents identity information being communicated to the Identity Reader.
Element 40 represents medical condition data communicated to the screening medical condition reader.
Element 41 represents precision medical condition data communicated to the precision medical reader.
Element 42 represents the database and data collected: Name or ID number.
Element 43 represents the database and data collected: Date/Time.
Element 44 represents the database and data collected: name of organization/location, entrance number, latitude/longitude.
Element 45 represents the database and data collected; individual's health measurement collected by the precision medical instrument at enrollment or updated from multiple measurements collected over time.
Element 46 represents the database and data collected: established safety delta from enrollment or adjusted by actual data collected on the specific individual from the medical precision device.
Element 47 represents the database and data collected: the alert condition indicating the person should not be allowed access and should see a doctor.
Element 48 represents the database and data collected: individual's health measurement collected by the screening instrument at enrollment or updated from multiple measurements collected over time.
Element 49 represents the database and data collected: established alert delta from enrollment or adjusted by actual data collected on the specific individual by the screening medical instrument.
Element 50 represents the database and data collected: the alert condition indicating the person should proceed for a reading from the precision medical device.
Element 51 represents the database and data collected: the screening medical device measurement.
Element 52 represents the database and data collected: the precision medical device measurement.
Element 53 represents the database and data collected: the action allowed for individual after using ATMs.
Element 54 represents the database and data collected: the location of each ATMs entrance point.
Element 55 represents the database and data collected: the date-time the individual entered the specific ATMs entrance point.
Element 56 represents the database and data collected: if an Alert was indicated.
Element 57 represents the database and data collected: the type of Alert.
Element 58 represents the database and data collected: the name or ID number of the person at the ATMs entrance point seeking entrance.

Element 59 represents the database and data collected: the individual's normal precision instrument measured medical condition, for example body temperature.

Element 60 represents the database and data collected: the precision instrument's recent measurement of the individual that caused the medical instrument to alert.

Element 61 represents the database and data collected: the individual's current location.

Element 62 represents the database and data collected: the individual's previous location and the ATMs' readings at that site.

Element 63 represents the database and data collected: additional previous location.

Element 64 represents the database and data collected: Miscellaneous data to help evaluate the person's previous location and interactions with others.

DETAILED DESCRIPTION OF THE EXEMPLARY EMBODIMENTS

An exemplary embodiment of the ATM system overcomes the deficiencies of prior-art methods for vetting the identity and state-of-health of persons seeking entry into areas of restricted access. Reliably vetting the identity of the individual is necessary but insufficient by itself. Combining the two steps is necessary to properly vet an individual for access to or the ability to remain in areas of restricted access. Accurate identification of the individual is essential for properly vetting the state-of-health of the individual. Temperature measurements associated with a particular identity enable the ATM to overcome the weaknesses of prior-art systems and provides new capabilities not enabled by prior-art methods. An exemplary embodiment of the ATM system records health data collected at multiple visits to access entry points to enable establishment of normal health parameters as a function of time for that individual for sensors used and data collection locations of that person's body. An exemplary embodiment of the ATM system enables a time-history of health parameter data collected at various locations to be used to estimate the risk of exposure of a potential contagion to the individual and/or the risk of other persons being exposed to a potential contagion by the individual. The time history data thus collected by one or more ATM system in communication with a centralized processor enables tracking or prediction of the spread of illness in a geographic area, thus providing a level of protection of individuals and populations not previously available.

Figure 1:
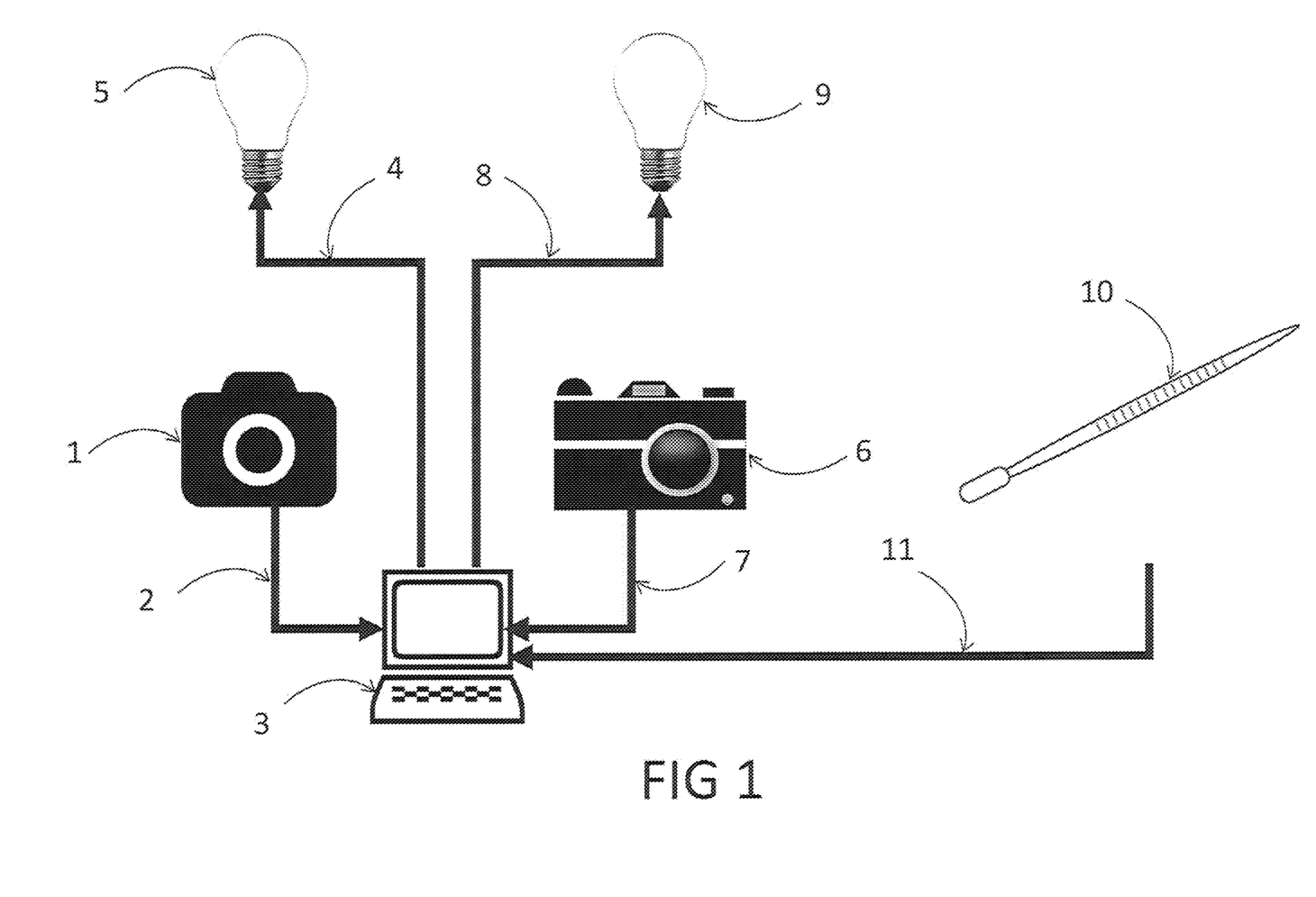
FIG. 1 is an overview of the components and connections of the Access and Temperature Monitoring system (ATMs).

As illustrated in FIG. 1, the system uses facial recognition to identify a person seeking access. To use this part of the system, a person seeking access looks into a camera connected to a computer running facial recognition software, and the software identifies the person based on facial similarity above a threshold. If the person is unknown or known but has no access to the restricted area, then the system does not indicate recognition, and this alerts an operator or disables automatic access control equipment such as an electronic door lock or a gate. If a known person who has authority to enter is recognized, then the system indicates success by turning on a light, and the person proceeds with a quick health assessment which, in this case, is a screening temperature measuring device such as an IR camera. If the person does not have an elevated temperature according to this screening temperature measuring device, then the system does not turn on a second light, and access is granted either by an operator or automatic access control equipment. However, if the screening temperature measuring device indicates that the person has an elevated temperature, then the system turns on a high temperature indication light to alert an operator and the person that the person's temperature should be checked using a more accurate, precision medical device before being admitted to the restricted area. In the situation where the temperature is found to be below a threshold, the individual will not be directed to seek medical attention. Similarly, if the temperature is found to be above a threshold, the person will be directed to seek medical attention.

There are many different methods of identifying a person, and all of them are appropriate for access control. For example, biometric readers can identify a person based on the uniqueness of a fingerprint, iris, face or other body part, voice or another physical characteristic, such as gait. Alternatively, a person might have a unique token of some kind that no one else has such as a smart card, or an RFID card or a card with a barcode or magnetic stripe. As another option, a person might know a secret of some kind that the system also knows but is unknown to any other person, for example a password or personal identification number. The system includes an identity reader that permits the system to identify a person seeking access by comparing the inputs provided by the person with database information obtained during enrollment, and further includes a process that creates database records for the set of persons who are known and authorized access.

FIG. 1 further depicts the ATMs system using temperature as the medical measurement to indicate a possible medical condition. The identification collector 1 can be a camera, RFID card reader, magnetic strip reader, Personal Identification Number (PIN) code, facial recognition, iris recognition, or any token or biometric that the entry point authorities wish to use to identify persons seeking access to a restricted area. The identity collection device 1 transmits the image or other identify data collected from the person seeking access to the system's computer 3 using a data communications device 2. The data communications device 2 may include cable (e.g., electronic conductors, optical fibers) or wireless communications (e.g., radio frequency, optics, magnetic or acoustic). The system's computer 3, processes the identification image or other identification data using matching algorithms. Search of the personnel database continues until a match is found or determines that the person is not in the database of individuals authorized access to the facility. The results are transmitted via 4 to the access approval light 5 indicating that the identity of the person has been validated and has authorization to access the restricted area. This light 5 represents other devices such auditory devices, door locks, SMS texts, or secondary alerts and datalinks. The screening sensor 6 will measure the person's medical condition and transmit it by communications link 7 to the computer 3. The computer 3 will compare the measurement data to the alert limit provided in the database for the identified individual. The results will be transmitted to the medical condition light 9 and displayed if under the minimum allowed temperature threshold or over the maximum allowed threshold. The medical condition status indicator 9 includes lights, auditory devices, door locks, SMS texts, or secondary alerts and datalinks. Should the individual's temperature reading exceed the individual's screening medical device maximum threshold in the database, the medical condition status light will indicate an over temperature signal and the individual will be asked to be tested by the is precision medical device 10. Results from the precision medical device 10 will be transmitted to the computer 3 for further actions. As an alternate exemplary embodiment, the identity collection device 1 and the contactless medical collection device 10 may be combined into a single collection device. For example, the image provided by a thermal camera may be used to establish the identity of the individual by means of facial recognition as well as providing the radiometric data to perform an assessment of state-of-health of the individual.

The system includes a database, which stores enrollment records including identities of persons authorized access to a restricted area as well as health measures taken when the person is healthy using both the quick health assessment method as well as the medically precise health assessment method.

Figure 2:
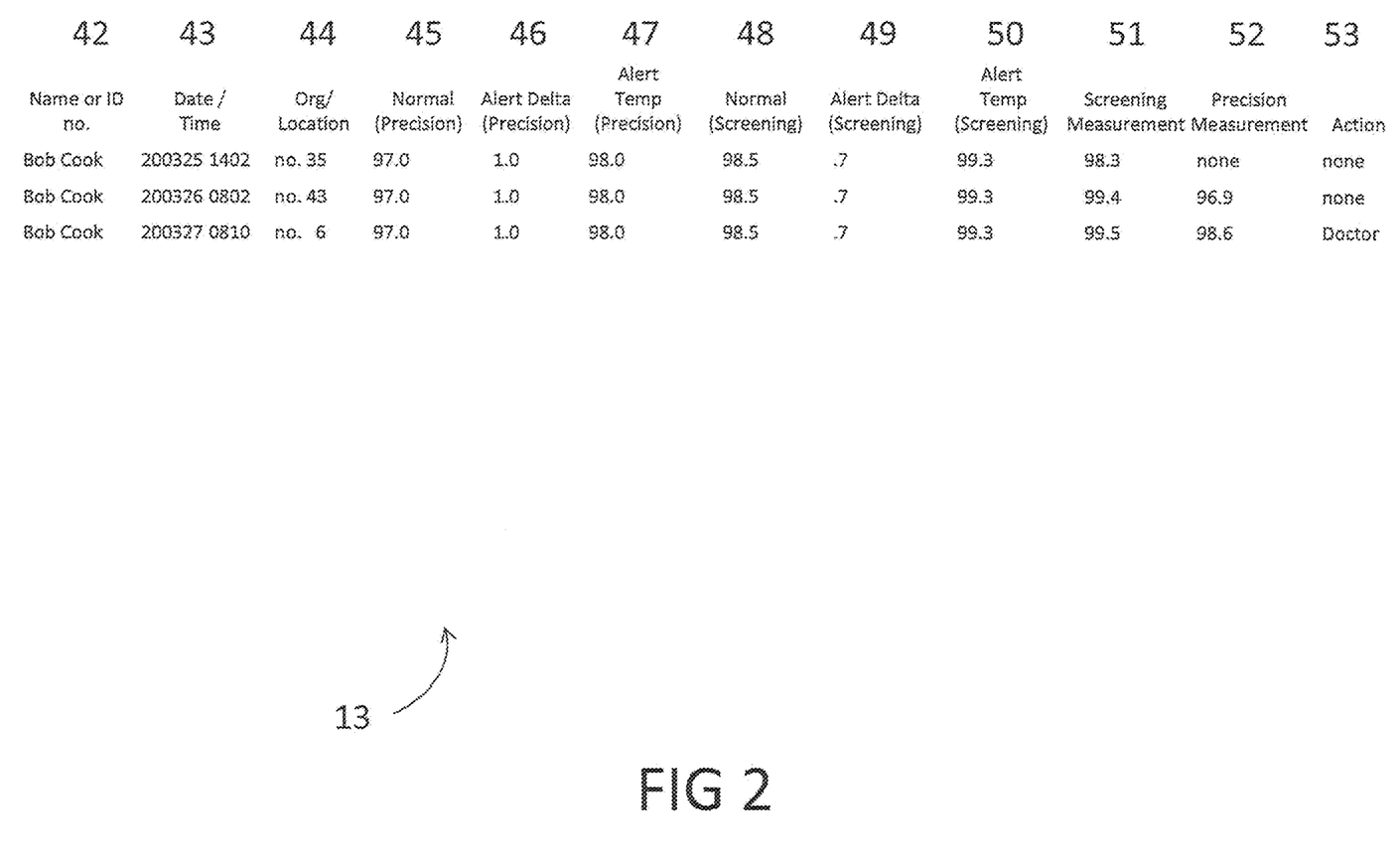
FIG. 2 illustrates a sample of the data in the system database.

FIG. 2 depicts the ATMs' database 13 that can be located on the system's central computer 3. One of the key novelties of the invention is evaluating the state-of-health of the individual seeking access to a facility contingent on the individual's baseline medical condition. The data that focused on this and would be desired to be collected during enrollment are the individual's name or identification number 42. In some cases, it is desirable to anonymize the database or otherwise disassociate a person's medical condition to the person's identity. In such a case, a number, template, code, PIN, token associated with the individual could be used. The date/time information 43 is important in tracking meaningful changes in a person such as elevated or fluctuating core temperature. The organization and location 44 are also important for data reduction. An artificial intelligent system could look for patterns to help distinguish between normal and abnormal reading for the individual, group, location, time-of-day, etc. Again, the goal is to detect abnormal medical conditions in order to prevent the spread to others and provide medical attention to those with abnormal or worsening medical conditions. Date/Time 43 and Organization/Location 44 are also important should a medical outbreak occur, as information will exist as to who, when and where they were, resulting in faster notification, verification, isolation, and treatment.

Temperature measurements obtained for an individual seeking access to an access point of a restricted area has the value of assessing the state-of-health of that individual for that moment in time. Many temperature measurements taken over a period of time for that individual has the added value of establishing the normal core temperature or range of temperatures for the individual. It is well known that core temperature for an individual can vary by as much as 1° F. (U.S. Pat. No. 9,470,584). Factors affecting variation of core temperature in an individual include circadian rhythm, reproductive cycles, season of year, etc. Age of the patient can introduce an additional 0.4° F. variability. Biometric identification of the individual provides greater assurance that the temperature measurements are properly-associated with the individual. The normal temperature of an individual for a particular sensor device and a particular measurement area can be computed from analysis of measurements taken over a period of time. Database items 45 and 48 represent the normal measured temperature for an individual using the precision and screening temperature sensors.

The precision measurement 45 is performed during enrollment using a precision medical device. When multiple temperature measurements from the precision medical device are available, entry point 45 will be updated from analysis of historical data. Data from this device is used to establish the alert delta 46 to compute the alert threshold 47. When this alert threshold is exceeded, the person needs to see a doctor. An example using temperature as the medical condition would be a person enrolls using the screening medical sensor 6 with a normal temperature is 98° F. It is important to note that this may not be the person's actual temperature as measured by the precision medical device 10. This temperature is less precise since it is contactless, and each person is structured a little differently, possibly responding differently to the screening sensor 6. The increment 49 may be selected with the knowledge of the system's accuracy, therefore a contactless indication of over a threshold alert 50 needs to be secondarily tested by the precision medical device 10. The screening temperature measurement 51 is recorded along with any precision device temperature measurements, 52 such that it can be available for further analysis.

There are many different measures and methods of quickly assessing the health of a person. For example, if the measure is elevated temperature, then the method may be a thermometer or digital thermometer under-the-tongue or in some other location on the body. An infrared thermometer may be used inside the ear or across the forehead. A screening infrared sensor may be aimed at a particular location on the body. Alternatively, an image from an infrared camera that identifies the highest temperature and location of the image may be used. As another example, the facial appearance of a person may indicate discomfort and illness, and this could be measured using an emotion estimation algorithm or color assessment applied to a face image. Any of these health assessment measures and methods apply, and the system includes at least one for a quick health assessment and one which is known to be medically precise.

Figure 3:
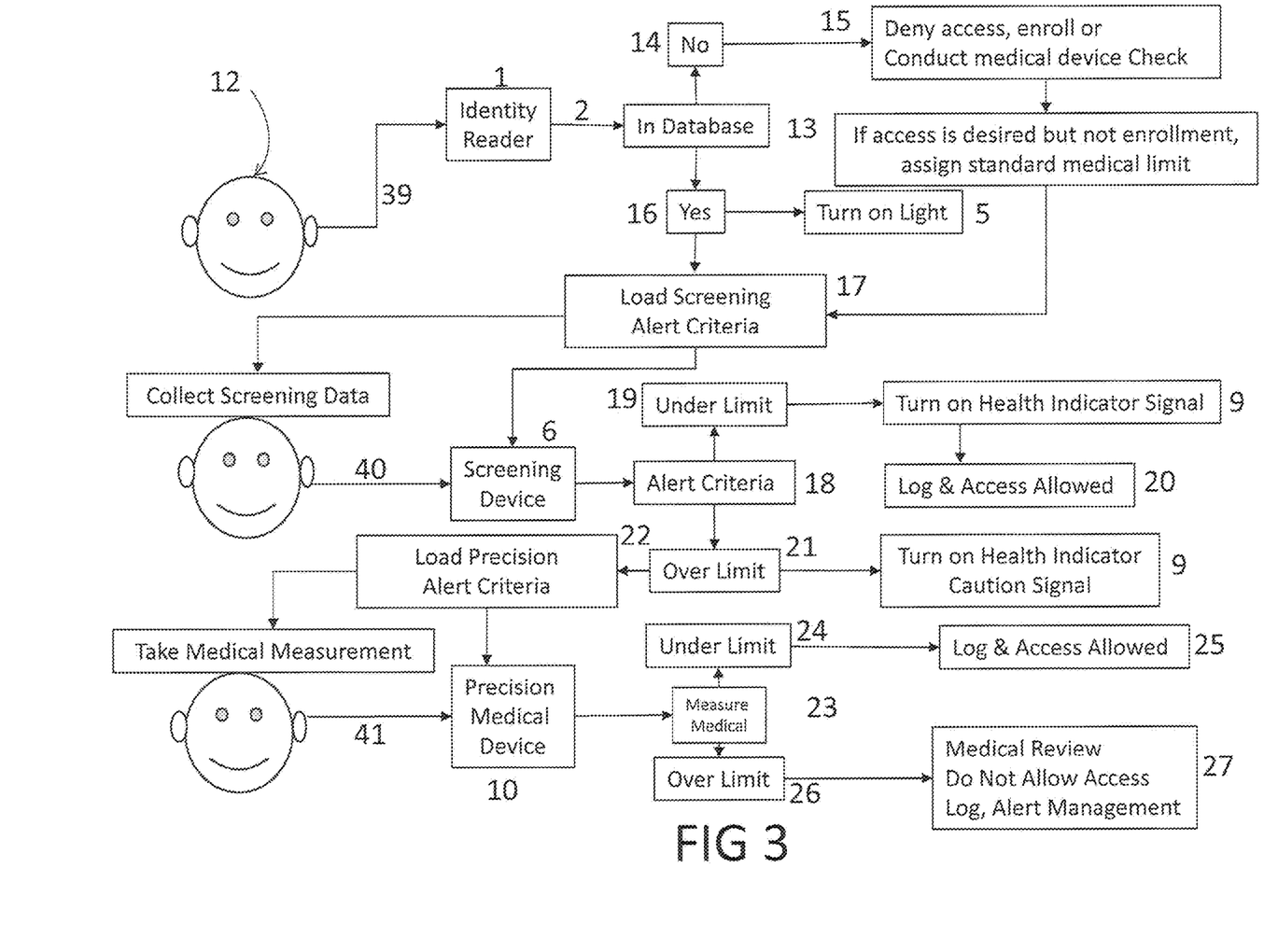
FIG. 3 illustrates the ATMs functioning and process.

FIG. 3 depicts a flow chart of the details of an exemplary embodiment. The individual seeking access 12 presents the identification biometric or token to the identity reader 1. The identity reader 1 converts the image or token 39 and through algorithms or look-up tables determines if the individual is in the database 13. If the individual 12 is not in the database 14 then the person 12 is given the option to enroll, or as a visitor, may just want to be checked by the screening reader 6 against a standard medical alert limit 18, or be denied access. If the individual's 12 identity is found in the database 16, the access light, signal, tone, message service, or other signal 5 is turned on. The alert criteria 17 for the individual is extracted from the database 13 for comparison against the measurement of the screening medical sensor 6. If the screening reader 6 results are under 19 the alert criteria 18, the health indication light, audio device, etc. would activate showing the individual is under the alert threshold. The individual has now completed the access criteria of (1) recognized as being in the system and (2) under the medical threshold indicating minimum likelihood of a problem. The individual would be allowed access and data logged 20.

If the individual's screening reader 6 temperature measurement indicates a condition above the alert criteria 21, the health indicator alert light, audio, etc. 9 would indicate a possible medical condition and the individual would be directed to a temperature measurement by the precision medical reader 10. The person's temperature measurement 41 would be read by the precision medical device 10 and compared 23 to the database alert threshold 47. If the precision measurement 23 is under the alert limit 24, the individual would be allowed access and the data would be logged 25. If the individual is over the limit 26, the individual would not be allowed access, all data logged, management alerted, and the individual would be referred to medical personnel 27.

In addition to providing useful information on the state-of-health of an individual based on repeated temperature measurements over a period of time and a particular location, there is also valuable information to be gained by collecting many temperature measurements over a period of time for that individual at many locations visited by that person. A database populated with times, dates, locations and core temperatures of an individual enables forensic reconstruction of the locations this individual may have been exposed to a contagious disease. Knowledge of such exposure can be used to assess the risk of exposure to others at locations this individual later visited.

Knowing the temperature history, geographic track of the individual and the state-of-health of populations visited by the individual has value in understanding the impact of places and people visited. The usefulness of the information temperature, time and location of many individuals has much more value. The value of the information scales with the number of individuals included in the database. The value of a database populated with the individuals of an organization such as a business or school having a single geographic location is much greater than that of a single individual. The value of database populated and shared by the organization is much greater when the organization is distributed over many locations. For a database populated and shared by many organizations at multiple locations (e.g., a Government agency), the information can be used to inform epidemiologic models to identify trajectories of infection and predict locations and times of future infections.

Figure 4:
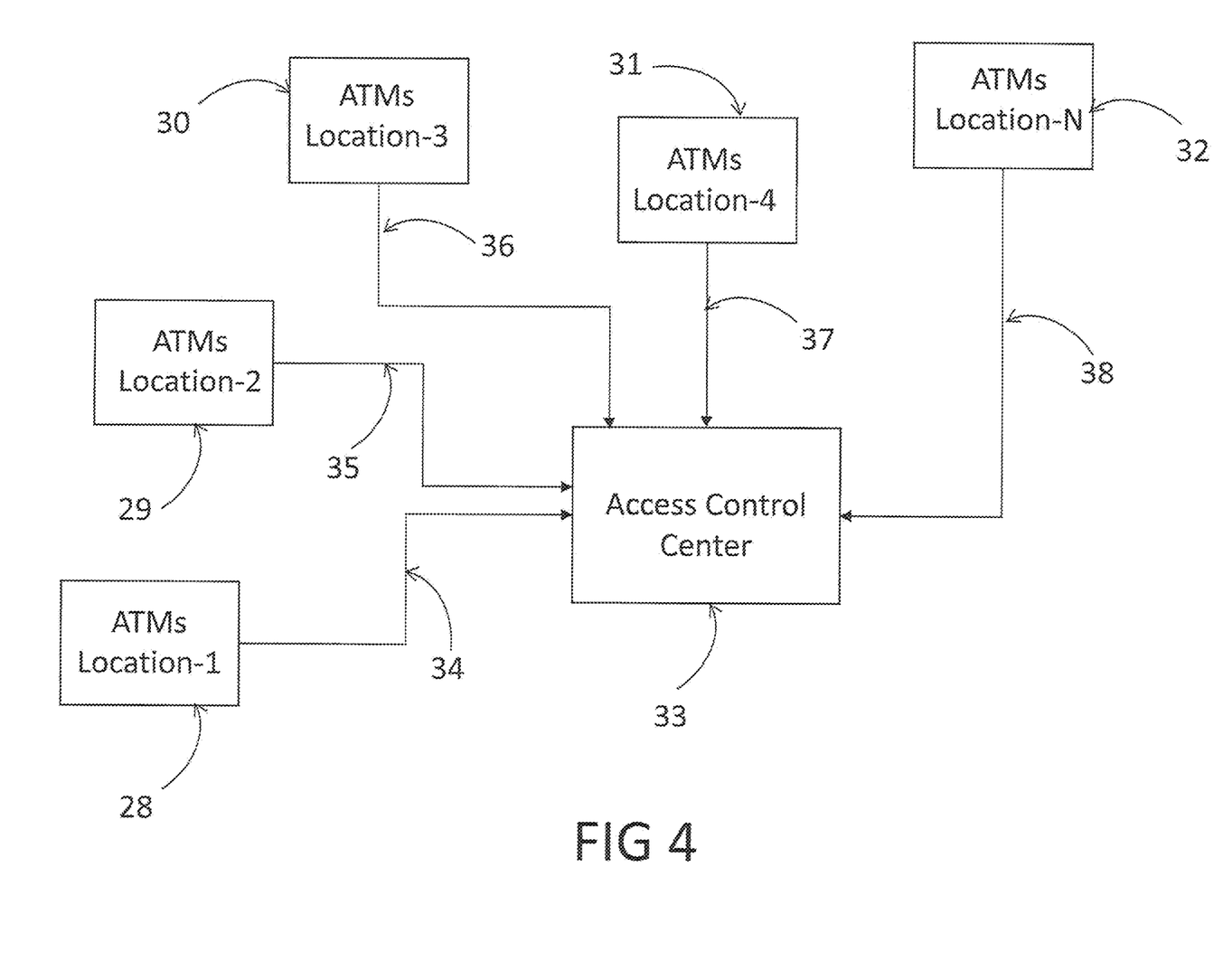
FIG. 4 illustrates linking the data from various ATMs locations to better analyze personnel data and sensor data at various locations as the same person enters different facilities.

FIG. 4 illustrates networking multiple ATMs locations into one centralized database to offer a level of individual tracking not possible in prior art. The Access Control Center 33 is the repository for all logs from each ATMs location. ATMs at various locations 28, 29, 30, 31, 32 transmit their enrollment data and data subsequently collected at access entry points 34, 35, 36, 37, 38, to the Access Control Center 33. Through the use of artificial intelligence, data reduction, and real-time monitoring, the pattern of various medical conditions can be quickly identified as isolated or growing. The ability to quickly identify personnel that have been exposed at a location is documented and would allow for a faster medical response by identifying persons that need to be quarantined. Effective Information Technology (IT) virus protection systems monitor overall data flow and focus on changes and abnormalities. This innovation's configuration presented in FIG. 4 would also reflect a similar approach by building an overall picture of human virus detection and growth.

Figure 5:
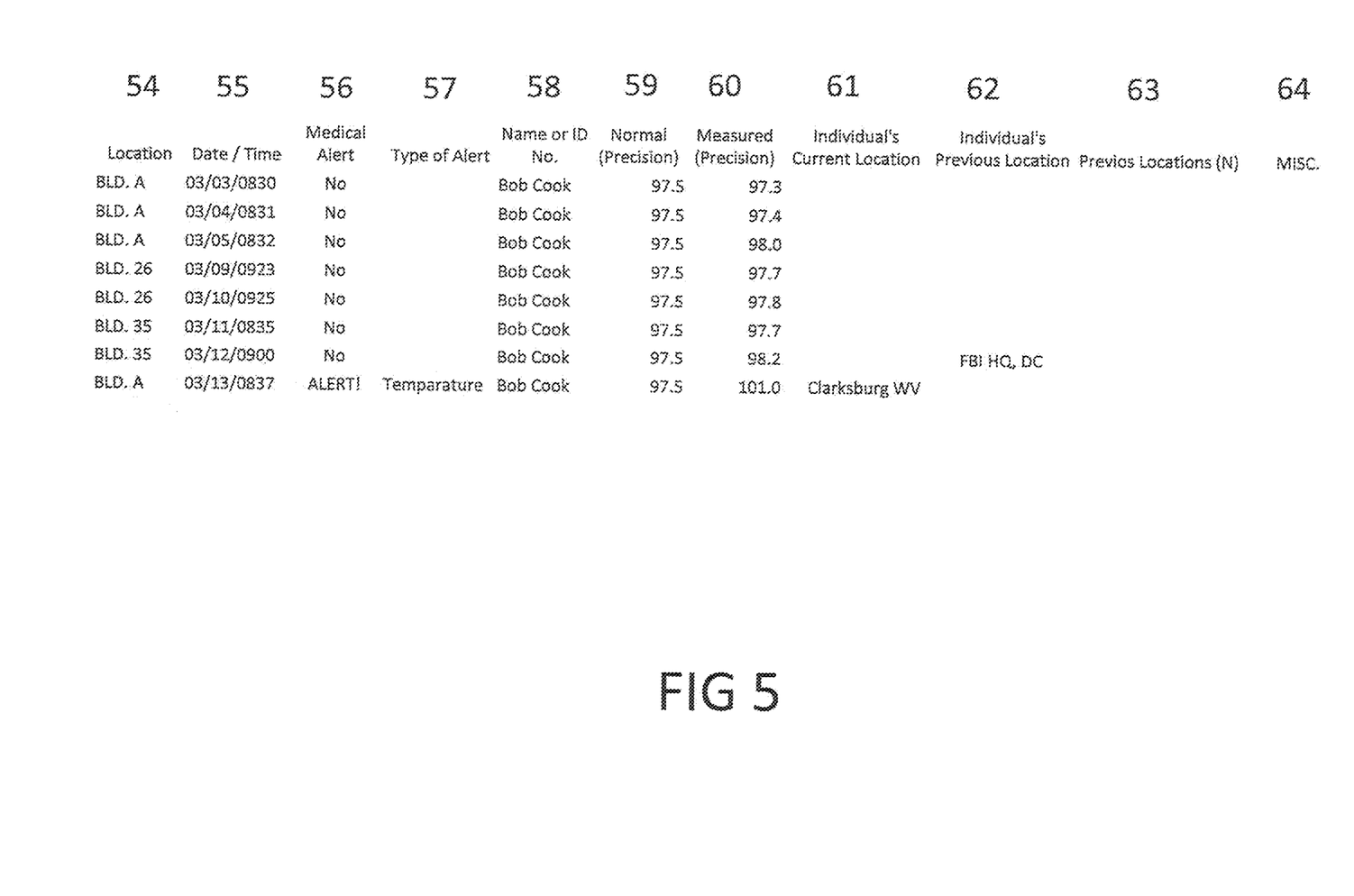
FIG. 5 illustrates a sample of data in the database of the Access Control Center.

FIG. 4 and FIG. 5 depict the centralization, oversight and analysis of the ACC 33 receiving real-time data centralization to real-time monitoring of a health problem. This real-time centralization will provide the ACC 33 the ability to identify and respond to a rapidly spreading virus. Monitoring the ATMs entry Date/Time group 55 at specific locations 54 will show a pattern of the individual's good health. When the individual's health condition changes and he/she enters an ATMs monitored portal, he will be detected and a medical alert 56 along with the type of medical alert 57 is provided to the facility. Medical alerts with respect to an individual can include abnormal temperatures, virus, drug use, alcohol consumption, mental alertness, and other medical and performance factors. Once an alert is indicated, the individual's normal medical standard 59 and the current measured medical condition 60 is provided to the ACC for rapid professional analysis. Providing specific alert data to the ACC and having a medical professional available, is an efficient way to inform the guard what to do at the specific location 54. The medical expert can also advise the alerted individual what medical actions the person should do. The medical expert can then look if other instances are being reported at other locations or does this appear to be an isolated incident. The medical expert can look at all the medical sensing data from the individual's immediate previous locations 62 to see if the medical condition was acquired at the location. The medical expert can focus on previous locations 63 to see if an outbreak is occurring. This embodiment would greatly assist the government in identification of rapidly spreading medical conditions and would assist in protecting workers in the facility from infected workers entering.

Other Exemplary Embodiments

Another exemplary embodiment is a Generalized Screening Approach with a different method of screening. In this approach, Artificial intelligence may also be utilized to improve or further automate the facilitation of contactless temperature acquisition for ATMs. Given a thermal sensor that is capable of being remotely controlled by digital signals, an artificial neural network model could be trained to identify regions of interest within the view of the sensor. Specifically, a model could be trained to identify the medial canthus or ethmoid sinus in real-time in addition to facial recognition. Thus, a thermal imager could be remotely controlled by the ATMs computer to identify and automatically save frames of these targets when in view.

An alternative embodiment of the ATMs relates to crowd monitoring. This exemplary embodiment enables screening of persons transiting an unobstructed passageway such as a sidewalk or hallway. In this embodiment, the identity collection device and the contactless medical collection device (a screening node) are covertly or overtly mounted in such a way to collect data from people transiting the passageway. Multiple screening nodes may be networked to provide enhanced awareness of larger areas of surveillance. Similar to the embodiment described for a gated access control point, the identity of each individual passing through the area is autonomously established, generally on-the-move. If the person is not authorized to be in that area, an alert is generated, and appropriate actions are taken to remove the unauthorized person from that area. Identity data associated with each person screened is stored in the ATMs database as well as time, date and location. In conjunction, a health assessment of each individual passing through the area is also autonomously conducted. Utilizing these datapoints including health metrics, time, date and location, a model of the normal health criteria for each individual is created for comparison with previous or later assessments. If the state-of-health of the individual is assessed to be outside accepted limits of variation, an alert is generated, and appropriate actions are taken to notify the affected person and/or proper authorities to administer secondary screening with a precision medical device. If the affected person poses a risk to others, the person may be removed from the area and the database of identities, time, date and location is used to establish which other persons were in close proximity with the affected person, Such information may be used to alert others of potential exposure to contagions. Multiple screening nodes may be networked to provide enhanced awareness of larger areas of surveillance. A networked system of screening nodes facilitates tracing the path of persons having diminished state-of-health and determine which other identities were possibly exposed to the affected person.

According to another exemplary embodiment, an emotion estimation algorithm is applied to a face image of a person as a health indicator of that person. Sickness causes distress in the body, and a sick person's facial expression reflects that distress. An emotion estimation algorithm can detect the facial expression of a sick person. Such an algorithm can even estimate how sick the person is because the facial expression becomes more pronounced the sicker the person is.

Although a number of different exemplary embodiments have been disclosed, other alternative systems would be readily apparent to one of ordinary skill in the art. The invention is not limited to the specifically disclosed exemplary embodiments, but rather by the appended claims.

What is claimed is:

1. An access and temperature monitoring system (ATMs) for identification of a person seeking access coupled with temperature monitoring automatically linked to said person's corresponding core temperature and alerting abnormalities, the system comprising:
   an individual identification system selected from a list of biometric, radio frequency identification, barcode, magnetic stripe cards, identification, cards, personal identification, numbers, other knowledge-based password or shared secret information, wherein the individual identification system stores individuals' identification, respectively, for identifying individuals via a matching process;
   a match indication system that is linked to said individual identification system which matches, via the matching process, said person seeking access to the individuals stored in the individual identification system;
   a primary screening core temperature measuring system that quickly measures the primary core temperature of said person seeking access without direct contact with said person, based upon said person being matched by the match indication system;
   a secondary medical precision core temperature measuring system which is separate from the primary screening core temperature measuring system;
   the secondary medical precision core temperature measuring system is configured to measure the temperature of said person seeking access through direct contact with said person to provide a greater medical level of confidence of said person's core temperature than said primary screening core temperature measuring system;
   a database containing a respective baseline initial enrolled core temperature taken from said primary screening core temperature measuring system and said secondary medical precision core temperature measuring system of said person seeking access;
   said database also contains separate selected alert levels for temperature readings from said primary screening core temperature measuring system and said secondary medical precision core temperature measuring system, respectively, of said person seeking access; and
   an alert indication system that provides an alert, in response to said secondary medical precision core temperature measuring system measuring said person's temperature exceeding above said person's database alert level temperature reading for the secondary medical precision core temperature measuring system, in response to the primary screening core temperature measuring system measuring said person's temperature exceeding above said person's database alert level temperature reading for the primary screening core temperature measuring system.

2. The access and temperature monitoring system (ATMs) of claim 1, further including facial recognition as the individual identification system.

3. The access and temperature monitoring system (ATMs) of claim 1, further including iris recognition as the individual identification system.

4. The access and temperature monitoring system (ATMs) of claim 1, further including identification systems selected from the list: radio frequency identification, magnetic strip cards, barcodes, PIN or other visual marking as the individual identification system.

5. The access and temperature monitoring system (ATMs) of claim 1, wherein the primary core temperature measuring device is an oral thermometer that works in direct contact with a person seeking access.

6. An access and temperature monitoring system (ATMs) that links ATMs together to provide all data to a nation-wide central access control center, the system comprising:
   more than one ATMs, each ATM comprising:
      an individual identification system selected from a list of biometric, radio frequency identification, barcode, magnetic stripe cards, identification, cards, personal identification, numbers, other knowledge-based password or shared secret information, wherein the individual identification system stores individuals' identification, respectively, for identifying individuals via a matching process;
   a match indication system that is linked to said individual identification system which performs the matching process to an identified person, corresponding to one of the individuals seeking access, to the individuals stored in the individual identification system;
   linking all ATMs to the nation-wide central access control center;
   the nation-wide central access control center includes a computer that monitors all personnel access, and primary medical conditions which are determined in a contactless fashion and stored in a database, in order to detect above threshold alerts relating to individuals being monitored by the system;
   the nation-wide central access control center in communication with:
      a primary screening core temperature measuring system that quickly measures the primary core temperature of said person seeking access, without contact with the person seeking access;
      a secondary medical precision core temperature measuring system which is separate from the primary screening core temperature measuring system, which involves direct contact with said person;
   said database containing a respective baseline initial enrolled core temperature taken from said primary screening core temperature measuring system and said secondary medical precision core temperature measuring system of said person seeking access;
   said database also contains separate selected alert levels for temperature readings from said primary screening core temperature measuring system and said secondary medical precision core temperature measuring system, respectively, of said person seeking access; and
   an alert indication system that provides an alert, in response to said secondary medical precision core temperature measuring system measuring said person's temperature exceeding above said person's database alert level temperature reading for the secondary medical precision core temperature measuring system, in response to the primary screening core temperature measuring system measuring said person's temperature exceeding above said person's database alert level temperature reading for the primary screening core temperature measuring system;

a computer trend model, neural network, expert system, or artificial intelligence system that detects abnormal core temperatures at each of the ATMs sites;

a communication link configured to be in communication with a trained medical expert that can rapidly interpret alert data and is configured to provide guidance to ATMs guards and alert the individual as to what to do next;

an alert process to notify the individuals seeking access when it has been determined that they were exposed to a possible contagious medical situation.

7. The Access and Temperature Monitoring system (ATMs) of claim 6, wherein the nation-wide or wide area central access control center's computer conducts trend analysis of said person's temperature, location, and date-time information, as well as identifying said individual seeking access.

8. The Access and Temperature Monitoring system (ATMs) of claim 6, further comprising conducting analysis of said person in relationship to other persons and locations to alert that said person was at a location at similar times with another person that tested positive for a virus.

9. The access and temperature monitoring system (ATMs) of claim 6, further comprising:
all of the ATMs are linked by a communications network.

10. The access and temperature monitoring system (ATMs) of claim 6, further comprising:
precision medical measuring devices which provide above and below threshold alerts which are transmitted to the central access control center.

11. The access and temperature monitoring system (ATMs) of claim 6, further comprising:
each ATMs including an identification control device and a medical condition measuring device which are combined into a single device.

* * * * *